United States Patent [19]

Freedman et al.

[11] Patent Number: 5,108,286

[45] Date of Patent: Apr. 28, 1992

[54] RETENTION MEANS FOR DENTAL IMPRESSION TRAYS

[76] Inventors: Richard S. Freedman; Roger Pierre, both of 1261 Deer Park Ave., North Babylon, N.Y. 11703

[21] Appl. No.: 652,517

[22] Filed: Feb. 8, 1991

[51] Int. Cl.$^5$ ............................................... A61C 9/00
[52] U.S. Cl. ............................................ 433/37; 433/47
[58] Field of Search ........................ 433/34, 37, 45, 47, 433/38

[56] References Cited

U.S. PATENT DOCUMENTS

| | | | |
|---|---|---|---|
| 1,763,553 | 6/1930 | Dennis | 433/37 |
| 3,534,475 | 10/1969 | Hilaire | 433/37 |
| 3,635,781 | 1/1972 | Guichet | 428/215 |
| 4,530,662 | 7/1985 | Andersson et al. | 433/37 |
| 4,768,951 | 9/1988 | Abiru et al. | 433/48 |
| 4,839,206 | 6/1989 | Waldenberger | 428/40 |
| 4,867,680 | 9/1989 | Hare et al. | 433/37 |

Primary Examiner—Gene Mancene
Assistant Examiner—Cindy A. Cherihetti
Attorney, Agent, or Firm—Bauer & Schaffer

[57] ABSTRACT

A dental impression tray is provided with mold compound retention means comprising a multilayer sheet having a thin, central layer of a plastic film, a layer of a selected adhesive applied on each surface of the film respectively, and a peel-away disposable foil cover on each layer of adhesive.

3 Claims, 1 Drawing Sheet

RETENTION MEANS FOR DENTAL IMPRESSION TRAYS

BACKGROUND OF THE INVENTION

The present invention relates to improvements in dental impression trays and, in particular, to retention means for use in combination with the dental impression trays having enhanced ability to hold the impression material and specially improved facility for separating the compound material from the mouth and the compound material from the tray after the impression has been made.

In order for a dentist to take the impression of a patient's jaw or part of the jaw, he employs a shovel-like tray filled with a plastic or maleable impression compound which solidifies in the mouth of the patient. After solidification, the tray and the solid compound is removed bodily from the mouth and used to cast or mold a replica of the patient's jaw or jaw parts for building replacement bridges and the like.

In order to manipulate the tray and the impression compound before, during, and after impression, the compound and the tray must both be chosen with several seemingly contradictory factors taken into account—namely:

1. The compound must be able to stick to the tray when first applied to it so that it will not slip or fall from the tray when being handled by the dentist.

2. The compound must also be sufficiently adherent to the tissues of the mouth and the gums so that every crack, fold, or crease in the mouth is transferred to the impressioned compound and the compound remains in that condition through the period of time necessary to provide sufficient solidification thereof.

3. On the other hand, the compound cannot stick or adhere too much to the mouth tissues so that it distorts or is damaged upon removal from the mouth.

4. The compound must also be easier to remove from the mouth than from the tray itself so that upon manipulation by the dentist to remove it from the mouth, it does not inadvertantly become separated from the tray itself.

Items 2 or 3 have been more or less successfully dealt with chemically in the creation of the impression compounds. On the other hand, Items 1 and 4 continue to present great problems to dentists or orthodontists because the interaction caused by the dissimilar, physical attributes of the chemical compound and the tray itself have not been successfully dealt with.

Many attempts have been made to provide more agreeable dental tray systems. For example, trays have been made of rigid or flexible metal or plastic. Preferably, such are made with holes to hold the compound. Adhesives, glues, jells, waxes are usually interposed between the surfaces of the tray and the impression compound. While some of these techniques solve one or more of the foregoing difficulties, they simultaneously exacerbate other problems or do not overall, solve all of the problems inherent in the use of different physical characteristics of compound and tray. Reference to U.S. Pat. Nos. 1,955,709; 2,703,452; 4,204,323; 4,530,662; and 4,907,966 may be made for a representative sample of the prior attempts at dealing with this problem.

It is, therefore, an object of the present invention to improve the use of the systems for dental impression compounds and trays.

It is an object to provide a system enhancing the retention of impression compounds on the tray for manipulation before, during, and after the dental impression as well as to provide for the proper separation of the compound from the mouth and the tray.

The foregoing object as well as other objects will be apparent from the following disclosure of the present invention.

SUMMARY OF THE INVENTION

According to the present invention, a dental impression tray is provided with mold compound retention means comprising a multilayer sheet having a thin, central layer of a plastic film, a layer of a selected adhesive applied on each surface of the film respectively, and a peel-away disposable foil cover on each layer of adhesive. The covers are sequentially removed, the first being removed so that the sheet may be secured to the surface of the tray and the second being removed to allow the molding compound to be secured to sheet itself. The adhesive coatings are each covered with a peel-way foil, which maintains the adhesive fresh during storage and ready for immediate use.

Preferably, the selected adhesive layers have the relative strengths sufficient to retain the impressioned compound in the said tray during handling and the impression stage, while allowing the solidified impression compound to be easily released from the tray once it is removed from the mouth.

Full details of the present invention are set forth within the following disclosure and are illustrated in the accompanying drawings.

IN THE DRAWINGS

DESCRIPTION OF THE PREFERRED EMBODIMENTS

Figure 1:
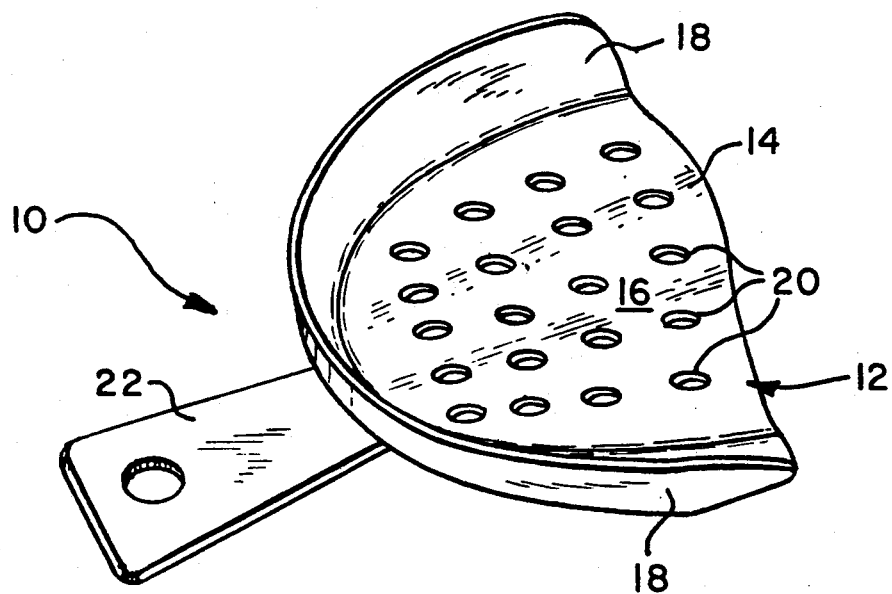
FIG. 1 is a perspective view of a dental impression tray.

As seen in FIG. 1, a conventional full upper jaw impression tray generally depicted by the numeral 10 is ilustrated. The tray 10 comprises a shovel-like body 12 defining a cavity for receiving the impression compound. The cavity has a bottom 14 conforming more or less to the arc of the teeth an undulate palate portion 16 and side wall means 18. The bottom, palate portion, and side walls are provided with openings 20, which serve normally to allow the impression compound to seep through when frist placed on the tray so as to form a firm grip between the compound and the tray. The openings 20, conveniently slots or holes, further serve later on to allow excess material to be forced out from between the tray and the patient's mouth. The number and arrangement of openings is not critical.

At present, the conventional impression trays such as those illustrated in FIG. 1 are made of suitable plastic such as polyacrylates, as well as other plastic material. In the past and still in use are metal trays made of stainless steel or similar metal. In general, such trays are provided with a handle 22 although sometimes this is also omitted. The impression compound may be plaster or most likely synthetic resinous compounds now more common in orthodontic practice.

The trays shown in FIG. 1 have been commonly sprayed with an adhesive material to ensure that the molding compound material is held securely during use. Such spraying of the adhesive material results in an uneven coating and leaves the holes 20 free for the impression material to seep through. The combination of the spay adhesive and the holes results in excess material falling into the mouth of the patient as well as the undersirable adhesion of the solidified compound to the tray, making it difficult to subsequently clean and sterilize the tray.

Figure 2:
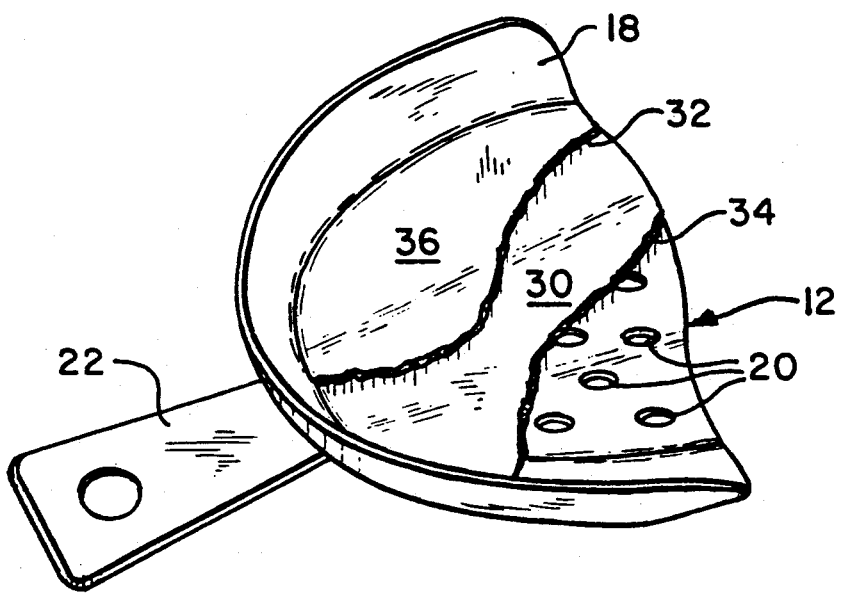
FIG. 2 is a similar view of the dental impression tray of FIG. 1 showing the application of the present invention to it.
Figure 3:
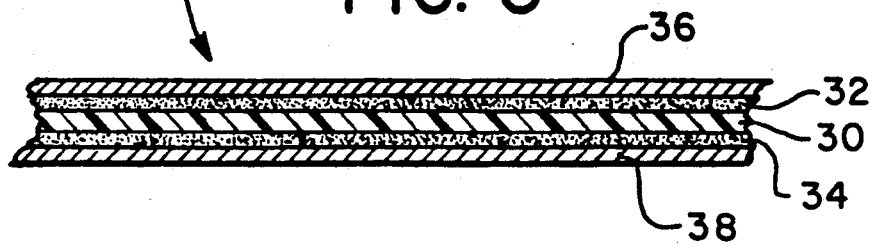
FIG. 3 is a partial sectional view of the retention means of the present invention.

As illustrated in FIGS. 2 and 3, the impression tray shown in FIG. 1 is provided with the system of the present invention. In accordance with the present invention, the tray 10 is covered with a unitary system comprising compound retention means 28 in the form of a carrier film 30 of thin, flexible plastic of high tensile strength covered on both its upper and lower sides with a layer of adhesive 32 and 34 respectively. The upper and lower surfaces 32 and 34 are provided with peel-away foils 36 and 38, respectively, which maintain the adhesive fresh and also keep the tray as a whole clean. The peel-away foil may be a sheet of paper treated on its undersurface with a coating of wax or plastic, ensuring its peelability from the adhesive without disturbing the uniformity of the adhesive layer. The entire system of the retention means consists of a very thin sheet, which when applied to the tray, does not add any appreciable thickness or distortion to the surface of the tray.

Since the adhesive is provided on both sides of the supporting sheet of plastic film and both sides are be covered with a peel-away foil, one adhesive layer may be exposed and placed on the surface of the tray while other adhesive layer is kept covered with the foil until the compound is to be applied to it. In this manner, the tray may be maintained covered during storage without harm to the adhesive. The dentist or orthodontist may purchase trays premade with the retention sheets for his own stock, or he may prepare his own as needed by buying a roll of double-sided adhesive sheet formed according to the present invention, from which he may cut sections to conform to the tray he is using. The conformed sections of the sheet may be applied to the tray just prior to its use. Also, the retention means of the present invention may be made in shaped form, conforming to one or more of the commonly used trays and supplied in bulk to the dentist in this cup-like or shovel-like configuration.

The construction of the double-sided adhesive sheets or peel-away foils are well known. Reference to the products of the Minnesota Mining and Minerals Company (3M) may be made. Conventional dental tray adhesives, either organic or latex, may be used as well as other adhesives not now suitable for use in the conventional systems because of rapid drying or other difficulties in application.

Adhesives may be chosen from the conventionally known adhesives for the desired characteristics for each of the layers. A separate adhesive can be selected for adherence with sufficient strength to the tray as well as to the molding compound. Thus, the adhesives can be chosen to provide optimum advantages for use. The covering foil may be color-coded or otherwise provided with indicia indicating proper placement with respect to the tray and compound.

Use of the retention means of the present invention may effect a change in the construction of the tray as such trays need no longer be made with holes and slots to grasp the mold compound. Excess mold compound does not have to be used to ensure a proper impression. The tray is kept cleaner in the mouth during impression, and the holes need not be scraped clean in order to prepare the tray for subsequent sterilization.

The present invention may take various forms and modifications and may undergo changes in size, color, or the like. The invention is easily adaptable in use to any shape of tray, whether for a full or partial mouth structure. Therefore, it is intended that the foregoing disclosure be taken as illustrative and not limiting of the invention.

What is claimed is :

1. In combination with a dental impression tray having a substantially rigid body having a bottom and upstanding outer walls defining a cavity in the shape at least of a portion of the mouth and jaw for receiving impression molding materials, retention means for holding said molding material in said cavity in the mouth and upon separation from said mouth, said retention means comprising a sheet consisting of a central carrier film a layer of selected adhesive applied on each surface of said film, and a peel-away foil cover disposed over each adhesive layer, one of said covers being removable to secure said sheet to the surface of said impression tray, and the other one of said covers being removable on application of the molding compound to said tray, the adhesive layer to be in contact with the surface of said tray being selected to have an enhanced holding strength with respect to the tray than the holding strength of the adhesive layer selected to be in contact with the molding compound relative to the compound, both of said adhesive layers having a holding strength preventing the separation of said adhesives from said central carrier.

2. The dental impression tray according to claim 1, wherein the adhesive coating is a latex adhesive coating and the impression material is a plaster.

3. The dental impression tray according to claim 1, wherein the impression material is polyacrylate plastic.

* * * * *